United States Patent
Singh et al.

(10) Patent No.: US 12,154,039 B2
(45) Date of Patent: Nov. 26, 2024

(54) MACHINE LEARNING FRAMEWORKS UTILIZING INFERRED LIFECYCLES FOR PREDICTIVE EVENTS

(71) Applicant: Optum Technology, Inc., Eden Prairie, MN (US)

(72) Inventors: Rama Krishna Singh, Noida (IN); Priyank Jain, Noida (IN); Ravi Pande, Noida (IN)

(73) Assignee: Optum Technology, Inc., Eden Prairie, MN (US)

( * ) Notice: Subject to any disclaimer, the term of this patent is extended or adjusted under 35 U.S.C. 154(b) by 1014 days.

(21) Appl. No.: 17/121,104

(22) Filed: Dec. 14, 2020

(65) Prior Publication Data
US 2022/0188664 A1  Jun. 16, 2022

(51) Int. Cl.
G06N 5/04 (2023.01)
G06F 18/214 (2023.01)
G06N 20/00 (2019.01)
G16H 10/60 (2018.01)

(52) U.S. Cl.
CPC .............. *G06N 5/04* (2013.01); *G06F 18/214* (2023.01); *G06N 20/00* (2019.01); *G16H 10/60* (2018.01)

(58) Field of Classification Search
None
See application file for complete search history.

(56) References Cited

U.S. PATENT DOCUMENTS

| | | | |
|---|---|---|---|
| 8,265,950 B2 | 9/2012 | Howe et al. | |
| 8,301,468 B2 | 10/2012 | Lutgen et al. | |
| 8,346,577 B2 | 1/2013 | Hogan et al. | |
| 9,026,551 B2 | 5/2015 | Drennan, III | |
| 10,325,020 B2 | 6/2019 | Burke et al. | |
| 10,535,430 B1* | 1/2020 | Fischer | G16H 40/20 |
| 2014/0046696 A1 | 2/2014 | Higgins et al. | |
| 2019/0108915 A1* | 4/2019 | Spurlock, III | G06Q 10/10 |
| 2019/0221312 A1 | 7/2019 | Al Hasan et al. | |
| 2019/0340487 A1 | 11/2019 | Aggarwal et al. | |
| 2020/0027531 A1 | 1/2020 | White et al. | |
| 2020/0027560 A1 | 1/2020 | Ling et al. | |

OTHER PUBLICATIONS

Christensen et al ("Machine Learning Methods for Disease Prediction with Claims Data" 2018) (Year: 2018).*
Cai et al ("Medical Concept Embedding with Time-Aware Attention" 2018) (Year: 2018).*
Yadav et al ("Mining Electronic Health Records (EHRs): A Survey" 2018) (Year: 2018).*

(Continued)

*Primary Examiner* — Lut Wong
(74) *Attorney, Agent, or Firm* — Alston & Bird LLP

(57) ABSTRACT

There is a need for more accurate and more efficient predictive data analysis steps/operations. This need can be addressed by, for example, techniques for efficient predictive data analysis steps/operations. In one example, a method includes mapping a primary event having a primary event code to a related subset of a plurality of candidate secondary events by at least processing one or more lifecycle-related attributes for the primary event code using a lifecycle inference machine learning model to detect an inferred lifecycle for the primary event.

17 Claims, 12 Drawing Sheets

(56) References Cited

OTHER PUBLICATIONS

Kalyan et al ("SECNLP: A survey of embeddings in clinical natural language processing" 2019) (Year: 2019).*

Choi, Edward et al. "Multi-Layer Representation Learning For Medical Concepts," arXiv:1602.05568v1, Feb. 17, 2016, (20 pages). DOI: https://arxiv.org/pdf/1602.05568.pdf.

Kalyan, Katikapalli Subramanyam et al. "SECNLP: A Survey of Embeddings In Clinical Natural Language Processing," Journal of Biomedical Informatics, vol. 101, No. 103323, Jan. 2020, pp. 1-21, (available online Nov. 8, 2019). DOI: 10.1016/j.jbi.2019.103323.

Kartchner, David et al. "Code2Vec: Embedding and Clustering Medical Diagnosis Data," In 2017 IEEE International Conference On Healthcare Informatics (ICHI), Aug. 23, 2017, pp. 386-390. DOI: 10.1109/ICHI.2017.94.

Zappa, Diego et al. "Text Mining In Insurance: From Unstructured Data To Meaning," Feb. 2019, (30 pages). Available online: https://www.researchgate.net/profile/Gian_Paolo_Clemente/publication/330969684_Text_Mining_in_Insurance_From_Unstructured_Data_to_Meaning/links/5c6813064585156b5701456e/Text-Mining-in-Insurance-From-Unstructured-Data-to-Meaning.pdf.

Zhong, Qiu-Yue et al. "Medical Concept Representation Learning from Claims Data and Application to Health Plan Payment Risk Adjustment," arXiv preprint arXiv:1907.06600, Jul. 15, 2019, (4 pages). DOI: arxiv.org/pdf/1907.06600.pdf.

* cited by examiner

402B

| Predictor (X) | | | | Estimated Value (Y) |
|---|---|---|---|---|
| ICD9 BODY PART | GENDER | Member Age | ... | Predicted values (Y-estimate) |
| Non-Hit | F | 30 | ... | 99.00 |
| Upper Arm | F | 14 | ... | 71.51 |
| HEAD | M | 3 | ... | 56.23 |
| Non-Hit | M | 32 | ... | 99.13 |
| Non-Hit | F | 15 | ... | 99.04 |
| Unspecified | F | 21 | ... | 108.27 |
| UNSPECIFIED | M | 5 | ... | 108.87 |
| Non-Hit | M | 60 | ... | 99.06 |
| Non-Hit | M | 30 | ... | 99.13 |
| Lower Leg | F | 59 | ... | 57.82 |
| Non-Hit | F | 40 | ... | 99.00 |
| Neck | F | 43 | ... | 43.17 |
| Non-Hit | F | 56 | ... | 98.97 |
| Trunk/Chest | F | 42 | ... | 55.03 |
| Non-Hit | F | 2 | ... | 99.06 |
| Back | M | 4 | ... | 84.04 |
| Non-Hit | F | 42 | ... | 99.06 |
| Non-Hit | F | 42 | ... | 98.99 |
| Non-Hit | F | 33 | ... | 99.00 |
| Non-Hit | F | 33 | ... | 99.01 |
| Non-Hit | F | 33 | ... | 99.00 |
| Neck | F | 35 | ... | 43.14 |

701 = Predictor (X); 702 = Estimated Value (Y)

FIG. 7

|       | ICD-1 | ICD-2 | ICD-n | RxUI-1 | RxUI-2 | RxUI-3 | CPT-1 | CPT-2 | CPT-n |
|-------|-------|-------|-------|--------|--------|--------|-------|-------|-------|
| CPT-n | 0 | 0 | 0 | 5 | 6 | 4 | 0 | 0 | 0 |
| CPT-2 | 0 | 0 | 0 | 4 | 3 | 2 | 0 | 0 | 0 |
| CPT-1 | 0 | 0 | 0 | 2 | 1 | 3 | 0 | 0 | 0 |
| RxUI-3 | 7 | 3 | 2 | 5 | 3 | 0 | 3 | 2 | 4 |
| RxUI-2 | 2 | 3 | 1 | 2 | 0 | 3 | 1 | 3 | 6 |
| RxUI-1 | 1 | 2 | 4 | 0 | 2 | 5 | 2 | 4 | 5 |
| ICD-n | 0 | 0 | 0 | 4 | 1 | 2 | 0 | 0 | 0 |
| ICD-2 | 0 | 0 | 0 | 2 | 3 | 3 | 0 | 0 | 0 |
| ICD-1 | 0 | 0 | 0 | 1 | 2 | 7 | 0 | 0 | 0 |

| MEMBER ID | Medical Claim | Corresponding Pharmaceutical Claims | |
|---|---|---|---|
| 12345678 | Medical Claim 1<br>Event Date: January 1 | Pharmaceutical Claim 1<br>Event Date: January 2 | Pharmaceutical Claim 2<br>Event Date: March 17 |

1200

FIG. 12

MACHINE LEARNING FRAMEWORKS UTILIZING INFERRED LIFECYCLES FOR PREDICTIVE EVENTS

BACKGROUND

Various embodiments of the present invention address technical challenges related to performing predictive data analysis steps/operations that are configured to generate direct mappings between indirectly related data records and disclose various innovative techniques for improving efficiency and/or reliability of predictive data analysis systems.

BRIEF SUMMARY

In general, embodiments of the present invention provide methods, apparatuses, systems, computing devices, computing entities, and/or the like for performing predictive data analysis steps/operations that are configured to generate direct mappings between indirectly related data records. In accordance with one aspect, a method for mapping a primary event having a primary event code to a related subset of a plurality of candidate secondary events is provided. In one embodiment, the method comprises: processing, by one or more computer processors, one or more lifecycle-related attributes for the primary event code using a lifecycle inference machine learning model to detect an inferred lifecycle for the primary event; determining, by the one or more computer processors, a filtered subset of the plurality of candidate secondary events, wherein each candidate secondary event in the filtered subset is associated with a candidate secondary event timestamp that falls within the inferred lifecycle; processing, by the one or more computer processors, the primary event code using a code co-occurrence inference machine learning model to detect a most co-occurring subset of a plurality of secondary event codes for the primary event; determining, by the one or more computer processors, the related subset based at least in part on each candidate secondary event of the plurality of candidate secondary events that is in a filtered subset and is associated with a candidate secondary event code that falls within the most co-occurring subset; and performing, by the one or more computer processors, one or more prediction-based actions based at least in part on the related subset.

In accordance with another aspect, an apparatus for mapping a primary event having a primary event code to a related subset of a plurality of candidate secondary events is provided, the apparatus comprising at least one processor and at least one memory including program code, the at least one memory and the program code configured to, with the processor, cause the apparatus to at least: process one or more lifecycle-related attributes for the primary event code using a lifecycle inference machine learning model to detect an inferred lifecycle for the primary event; determine a filtered subset of the plurality of candidate secondary events, wherein each candidate secondary event in the filtered subset is associated with a candidate secondary event timestamp that falls within the inferred lifecycle; process the primary event code using a code co-occurrence inference machine learning model to detect a most co-occurring subset of a plurality of secondary event codes for the primary event; determine the related subset based at least in part on each candidate secondary event of the plurality of candidate secondary events that is in the filtered subset and is associated with a candidate secondary event code that falls within the most co-occurring subset; and perform one or more prediction-based actions based at least in part on the related subset.

In accordance with yet another aspect, a computer program product computer program product for mapping a primary event having a primary event code to a related subset of a plurality of candidate secondary events is provided, the computer program product comprising at least one non-transitory computer-readable storage medium having computer-readable program code portions stored therein, the computer-readable program code portions configured to: process one or more lifecycle-related attributes for the primary event code using a lifecycle inference machine learning model to detect an inferred lifecycle for the primary event; determine a filtered subset of the plurality of candidate secondary events, wherein each candidate secondary event in the filtered subset is associated with a candidate secondary event timestamp that falls within the inferred lifecycle; process the primary event code using a code co-occurrence inference machine learning model to detect a most co-occurring subset of a plurality of secondary event codes for the primary event; determine the related subset based at least in part on each candidate secondary event of the plurality of candidate secondary events that is in the filtered subset and is associated with a candidate secondary event code that falls within the most co-occurring subset; and perform one or more prediction-based actions based at least in part on the related subset.

BRIEF DESCRIPTION OF THE DRAWINGS

Figure 1:
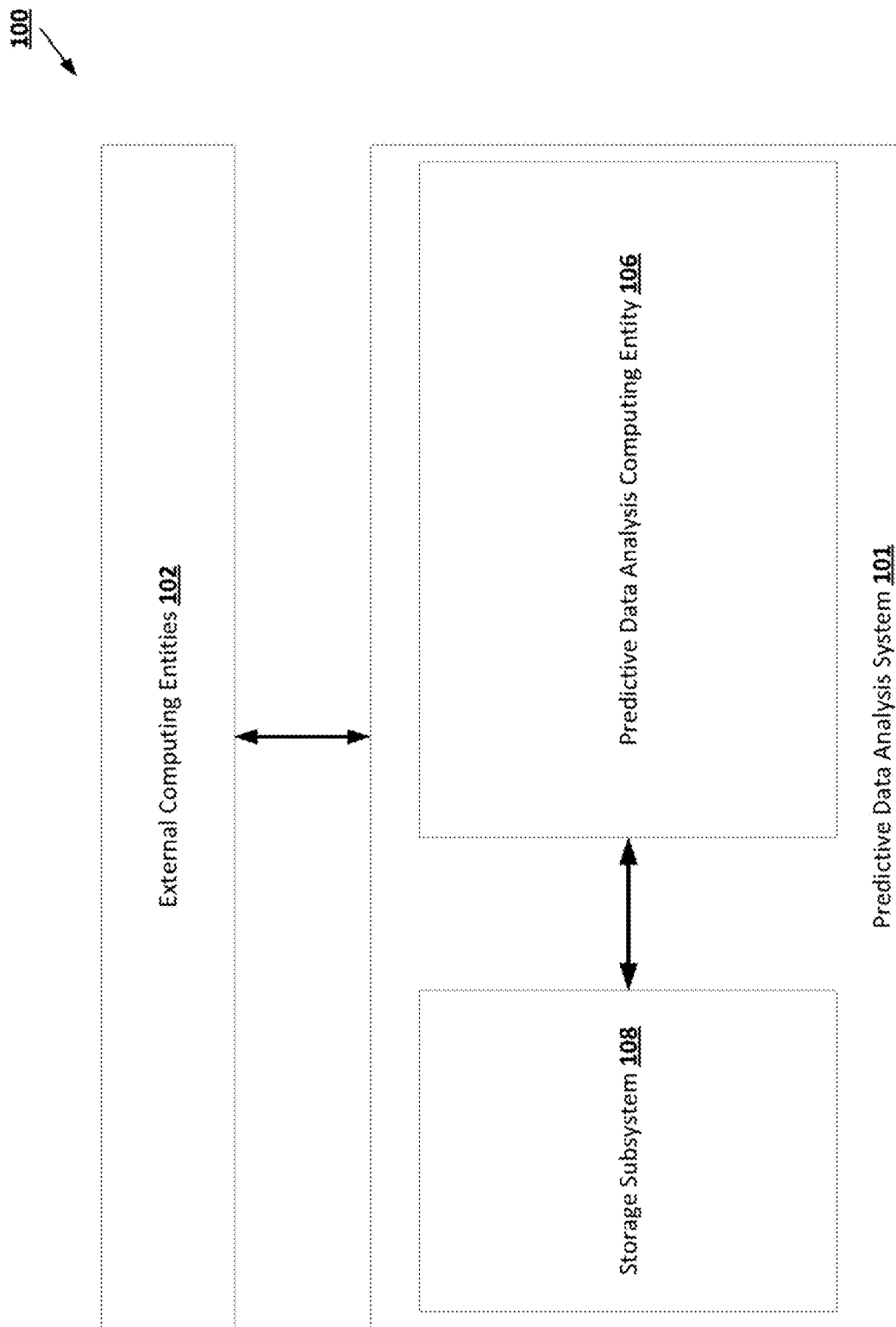
Figure 2:
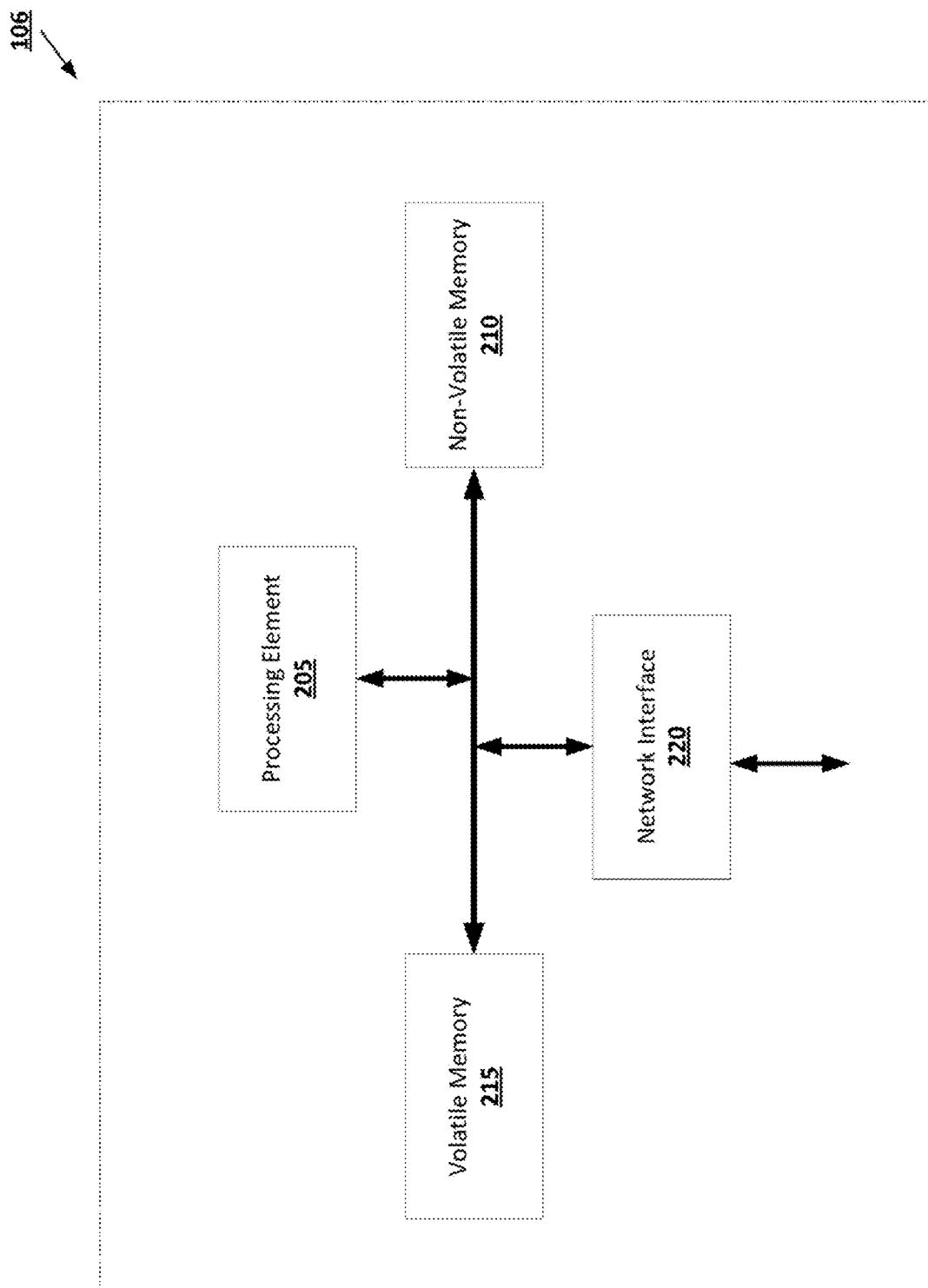
Figure 3:
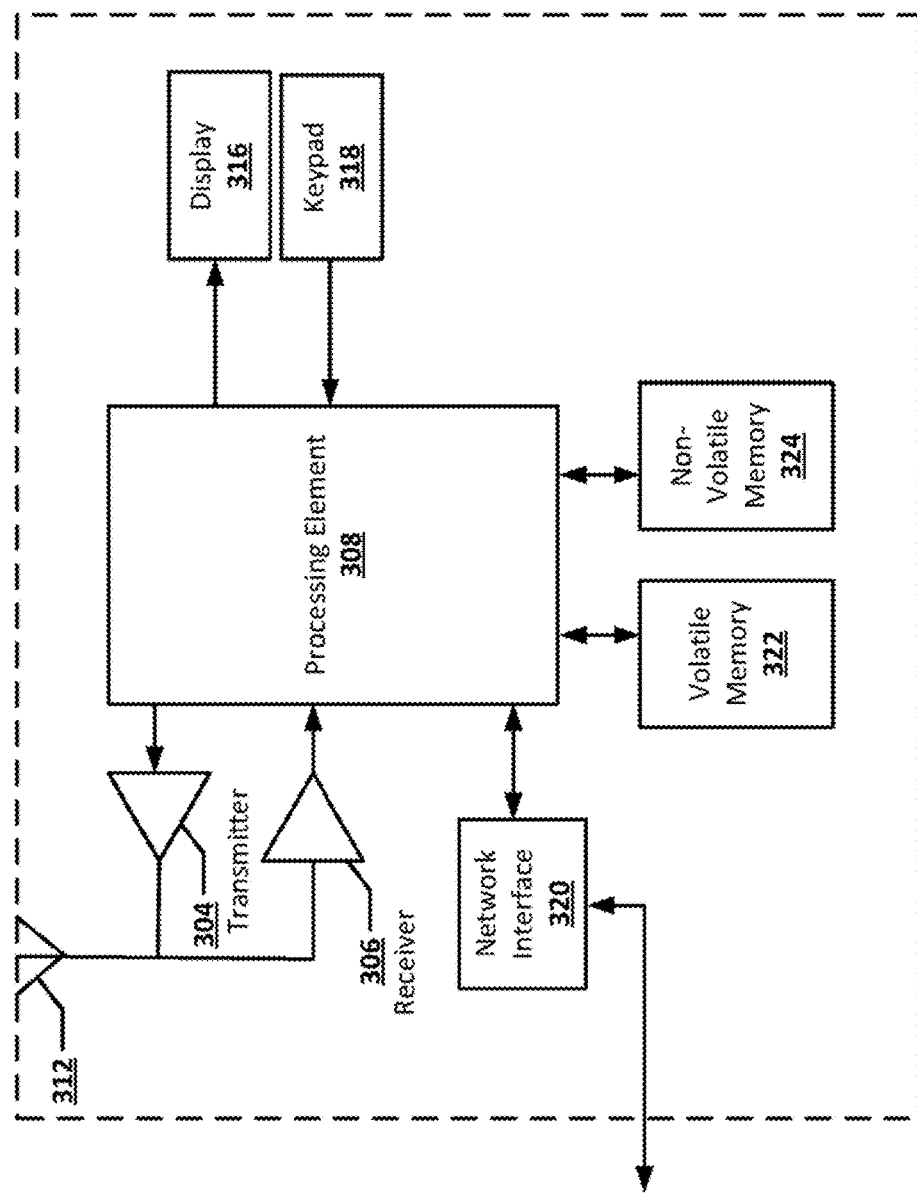
Figure 4:
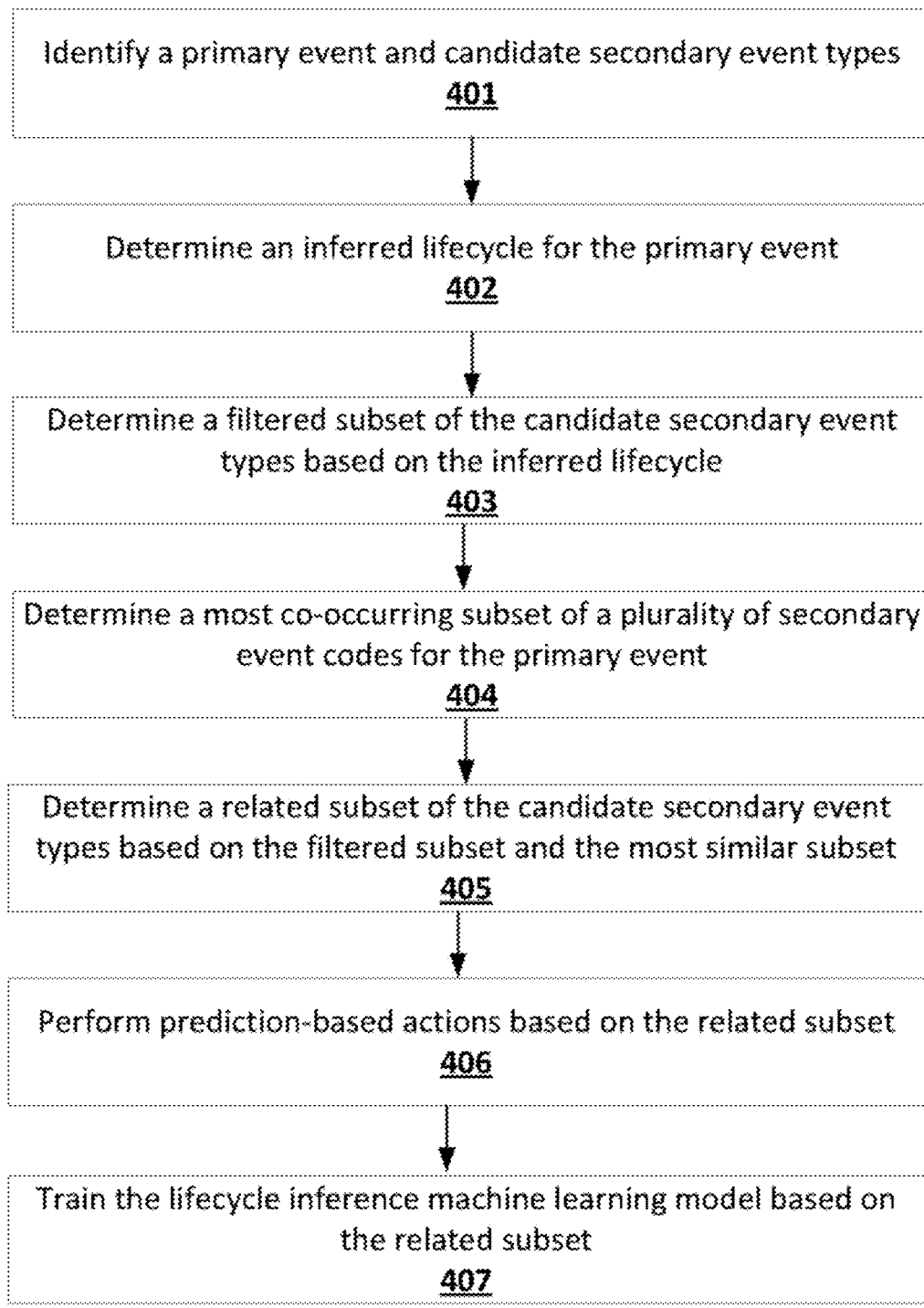
Figure 5:
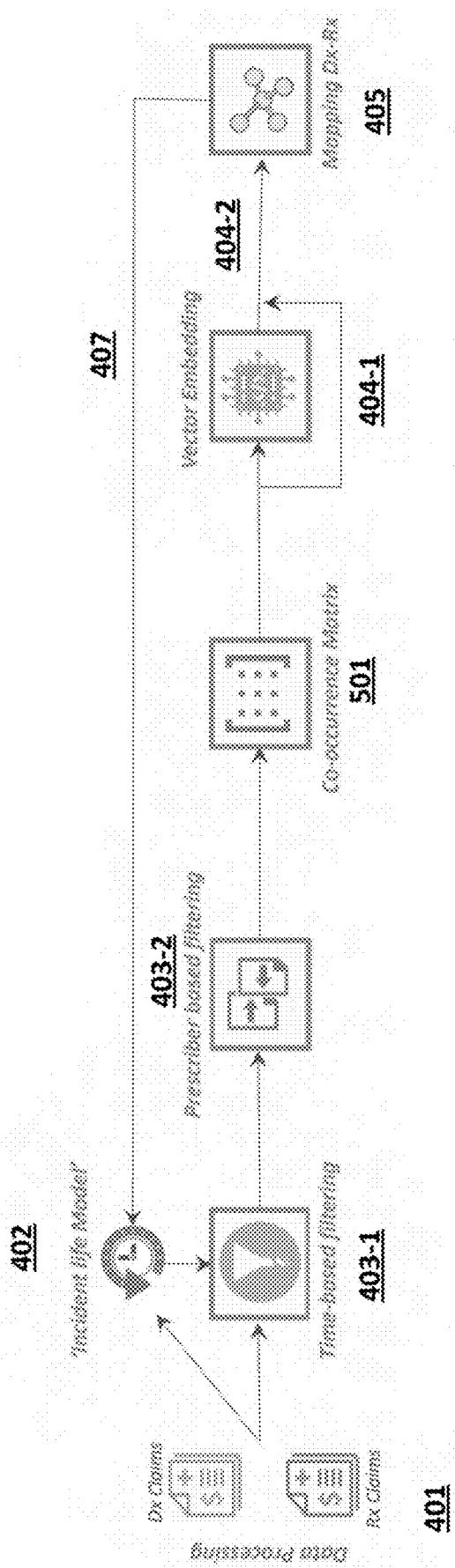
Figure 6:
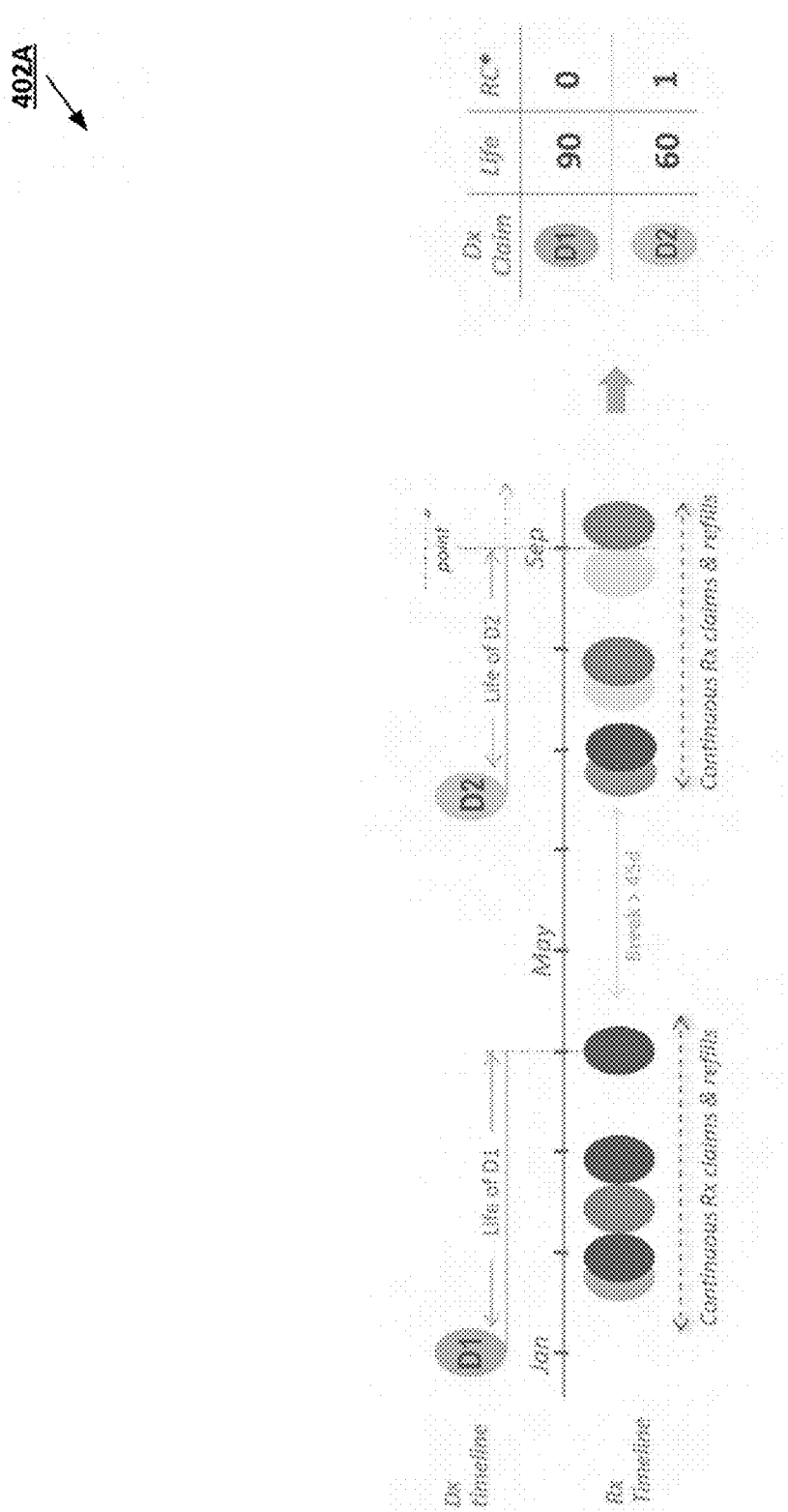
Figure 8:
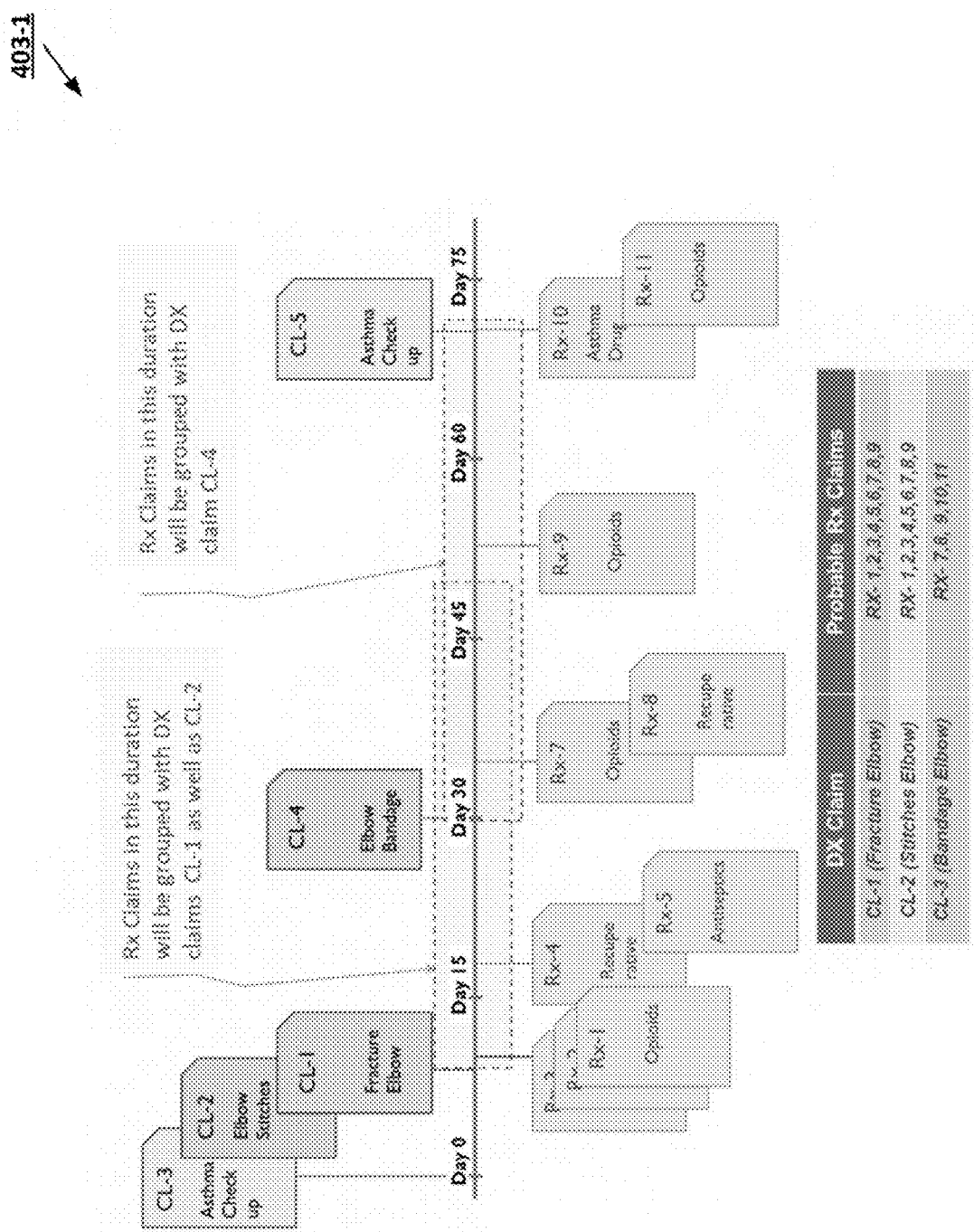
Figure 9:
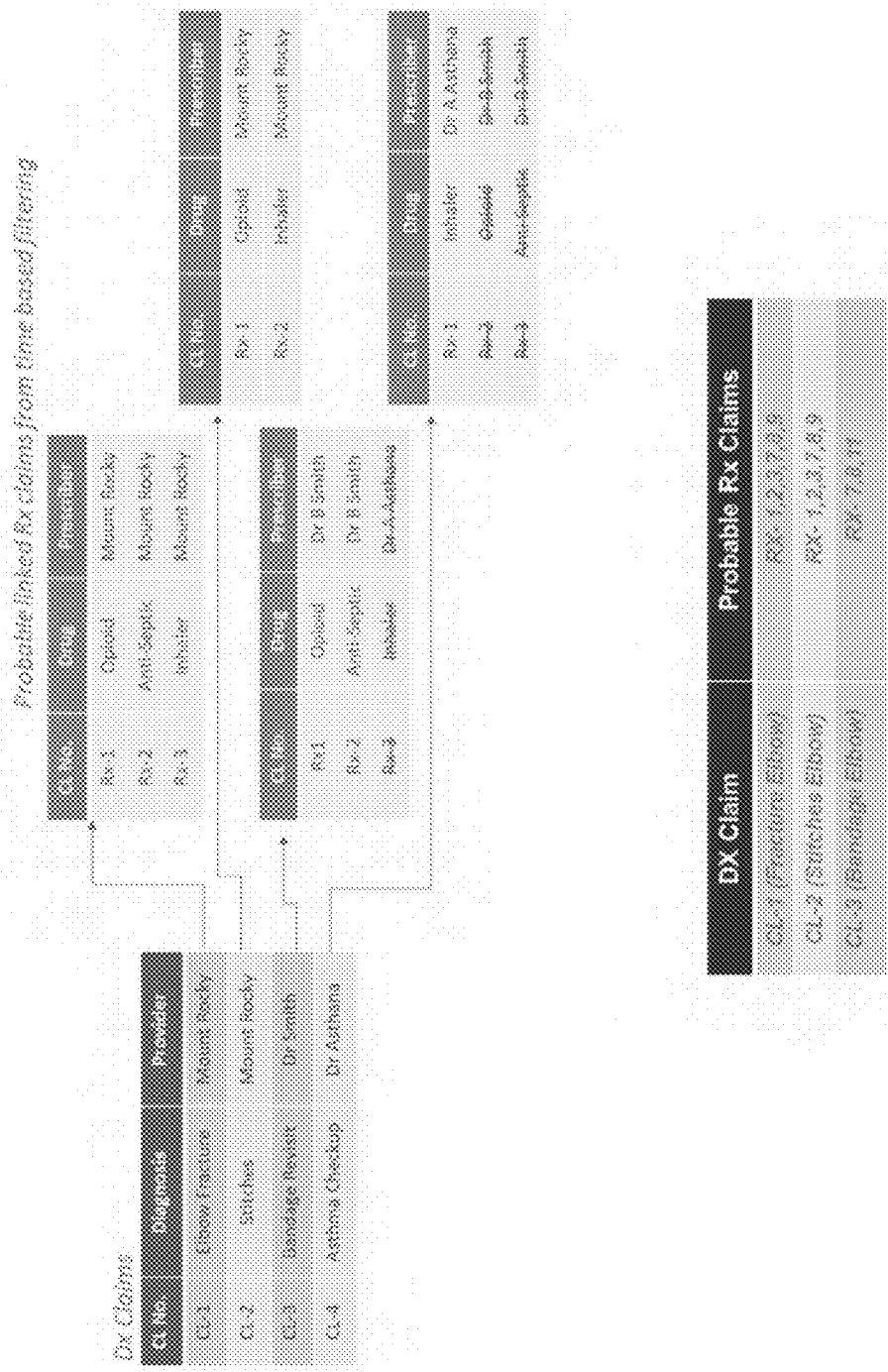
Figure 11:
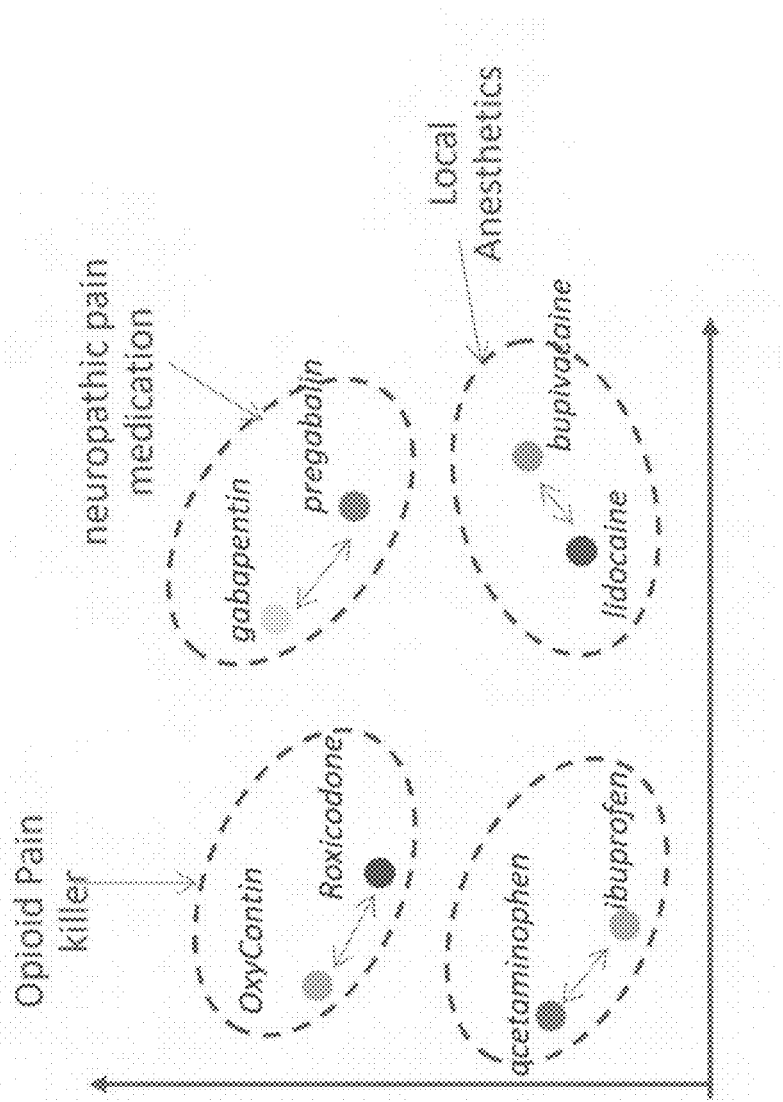

Having thus described the invention in general terms, reference will now be made to the accompanying drawings, which are not necessarily drawn to scale, and wherein:

FIG. 1 provides an exemplary overview of a system that can be used to practice embodiments of the present invention;

FIG. 2 provides an example predictive data analysis computing entity in accordance with some embodiments discussed herein;

FIG. 3 provides an example external computing entity in accordance with some embodiments discussed herein;

FIG. 4 provides a diagram of an example process for determining a related subset of a plurality of candidate secondary events with respect to a primary event having a primary event code in accordance with some embodiments discussed herein;

FIG. 5 provides an operational example of generating direct mappings between medical claims and pharmaceutical claims in accordance with some embodiments discussed herein;

FIG. 6 provides an operational example of generating an inferred lifecycle for a primary event given an insufficiently trained lifecycle inference machine learning model in accordance with some embodiments discussed herein;

FIG. 7 provides an operational example of training data for a lifecycle inference machine learning model in accordance with some embodiments discussed herein;

FIG. 8 provides an operational example of performing time-based filtering steps/operations in accordance with some embodiments discussed herein;

FIG. 9 provides an operational example of performing attribute-based filtering steps/operations in accordance with some embodiments disclosed herein;

FIG. 10 provides an operational example of a medical-claim-pharmacy-claim co-occurrence matrix in accordance with some embodiments discussed herein;

FIG. 11 provides an operational example of a multi-dimensional embedding space in accordance with some embodiments described herein; and FIG. 12 provides an operational example of a prediction output user interface in accordance with some embodiments discussed herein.

DETAILED DESCRIPTION

Various embodiments of the present invention are described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Advantages

Various embodiments of the present invention disclose techniques for performing predictive data analysis steps/operations that are configured to directly map indirectly related data records, techniques that are in turn configured to improve the efficiency of performing the noted predictive data analysis steps/operations and reliability of the generated results. Typically, predictive data analysis steps/operations are unable to directly map indirectly related data records (e.g., corresponding with a primary event and a plurality of candidate secondary events) in an efficient manner and are inadequate for cross-correlating data corresponding with different record types in a meaningful way. Additionally, existing techniques are time consuming and require a lot of computational resources. As a result, secondary data records that cannot be directly mapped to a primary event record may be underutilized in performing predictive data analysis steps/operations. There is a need for improved systems and methods configured to directly map indirectly related data records in an efficient manner. Thus, various embodiments of the present invention improve predictive analysis data steps/operations by cross-correlating different data record types efficiently and quickly. The inventors have confirmed, via experiments and theoretical calculations, that various embodiments of the disclosed techniques improve efficiency and accuracy of predictive data analysis systems and predictive data analysis relative to various state-of-the-art solutions by improving efficiency of cross-correlating indirectly-related data records.

Various embodiments of the present invention utilize predictive data analysis steps/operations (e.g., machine learning models, time-based filtering techniques, attribute-based filtering techniques and/or the like) in order to determine an inferred lifecycle for a primary event which can be utilized to directly map a related subset of a plurality of candidate secondary events to the primary event. Accordingly, accurate predictions can be generated by utilizing inferred mappings between indirectly-related data records and without overburdening available computational resources. Additionally the predictive data analysis techniques described herein do not require a time-consuming analysis of the underlying data in order to cross-correlate indirectly-related data records.

By facilitating efficient and reliable performance of predictive data analysis steps/operations through enabling inference of direct mappings between indirectly-related data records, various embodiments of the present invention improve data retrieval efficiency as well as data storage efficiency of various data storage systems. For example, by utilizing the techniques described herein, efficiency and reliability of search steps/operations by enabling faster and more reliable detection of cross-record relationships which can then be used to enhance the quality of generated search results. Furthermore, the techniques described herein enable faster and more accurate cross-correlation of disparate data record types. This in turn increases the efficiency and reliability of data retrieval steps/operations and/or data query processing steps/operations across various data storage systems, such as various data storage systems that act as a server devices in distributed client-server data storage architectures.

Accordingly, by utilizing some or all of the innovative techniques disclosed herein for performing predictive data analysis steps/operations, various embodiments of the present invention increase efficiency and accuracy of data storage steps/operations, data retrieval steps/operations, and/or query processing steps/operations across various data storage systems, such as various data storage systems that are part of client-server data storage architectures. In doing so, various embodiments of the present invention make substantial technical contributions to the field of database systems and substantially improve state-of-the-art data storage systems.

II. Definitions of Certain Terms

The term "primary event" may refer to a data object that describes a record of an occurred event in response to which occurred events pertaining to one or more secondary events occur. The primary event may be associated with a primary event timestamp indicating a timepoint associated with the primary event. An example primary event may be a recorded medical claim entry for a patient profile. The primary event may be associated with one or more primary event attributes, including a primary event code (e.g., a medical claim code, such as a diagnosis code, a procedure code, and/or the like).

The term "secondary event" may refer to a data object that describes a record of an event occurring in response to a primary event. The secondary event may correspond with a secondary event timestamp, indicating a timepoint associated with the secondary event and occurring subsequent to the timepoint of a corresponding primary event timestamp. An example secondary event may be a data object describing a recorded pharmaceutical claim entry for a patient profile. A secondary event may be associated with one or more secondary event attributes including a secondary event code (e.g., a pharmaceutical claim code).

The term "lifecycle inference machine learning model" may refer to a data object that describes steps/operations and/or parameters of a machine learning model that is configured to determine an inferred lifecycle (e.g., a time window, time-to-event and/or the like) with respect to a primary event. The steps/operations of the lifecycle inference machine learning model may lead to performing one or more prediction-based actions. The lifecycle inference machine learning model may be configured to iteratively process one or more lifecycle-related attributes corresponding with a primary event code in order to detect an inferred lifecycle for the primary event. The lifecycle inference machine learning model may be trained based at least in part on a ground-truth inferred lifecycle. The ground truth inferred lifecycle may be a data object describing one or more candidate secondary event timestamps for one or more candidate secondary events of a plurality of secondary events in a related subset. An example of a lifecycle inference machine learning model is an incident life machine learning model, a survival machine learning model, a time-to-event machine learning model, a regression-based proportional hazard machine learning model (e.g., Weibull model, Log-Normal model, Gamma model, Log-logistic model and/or the like) a convolutional neural network model, and/or the like. An example algorithm for a lifecycle inference machine learning model can be:

$$Ln(Y) = \beta_0 + \beta_1 x_1 + \beta_2 x_2 \ldots \beta_p x_p * Ln(\in)$$

In the above algorithm,

Y is the inferred lifecycle;

$x_0 \ldots x_p$ are lifecycle-related attributes and corresponding coefficients, $\beta_0 \ldots \beta_p$; and $\in$ is the error term assumed to have a particular parametric distribution.

The term "lifecycle-related attributes" may refer to a data object that describes one or more related attributes corresponding with a primary event (e.g., a medical claim entry), where the one or more related attributes are configured to be processed by a lifecycle inference machine learning model to generate an inferred lifecycle for the primary event. An example primary event may be a recorded medical claim entry for a patient profile. Example claim attributes for a recorded medical claim entry for a patient profile may be the subscriber number for the patient profile, the member identifier for the patient profile, the member demographic information/data (e.g., age, gender, co-morbidities and/or the like) for the patient profile, and/or the like.

The term "inferred lifecycle" may refer to a data object that describes a predicted time period for a primary event, where the predicted time period is estimated to include the secondary events associated with the primary event. In some embodiments, when a lifecycle inference machine learning model is deemed insufficiently trained (e.g., during an initial iteration of a predictive framework), the inferred lifecycle may be deemed to commence with a primary event timestamp and continue till a plurality of secondary events happen without a considerable time break (e.g., may terminate if there are no secondary events continuously for 45 days after the primary event timestamp. In some embodiments, when a lifecycle inference machine learning model is deemed sufficiently trained (e.g., during a post-initial iteration of a predictive framework), the inferred lifecycle may be determined by processing one or more lifecycle-related attributes for a corresponding primary event using a lifecycle inference machine learning model.

The term "filtered subset" may refer to a data object describing one or more candidate secondary events, each associated with a candidate secondary event timestamp that falls within an inferred lifecycle corresponding with a primary event, where the one or more candidate secondary events are determined at least in part by performing one or more filtering steps/operations and/or matching steps/operations with respect to all of the candidate secondary events that fall within the inferred lifecycle. Example filtering steps/operations include, without limitation, time-based and/or attribute-based filtering steps/operations. Example matching steps/operations include, without limitation, Levenshtein fuzzy matching, Soundex, a Smith Waterman algorithm, an ensemble approach and/or the like.

The term "code co-occurrence inference machine learning model" may refer to a data object that describes steps/operations and/or parameters of a machine learning model that is configured to process one or more primary event codes in order to detect a subset of a plurality of secondary event codes having high co-occurrences (i.e. that frequently occur with or after the primary event code on the timeline) with respect to the primary event codes. In some embodiments, the code co-occurrence inference machine learning model is first configured to determine a defined-size subset of a plurality of secondary event codes (e.g., a subset of three most co-occurring secondary event codes, which could be similar or dissimilar), wherein each secondary event code in the defined-size subset is deemed to have an above-threshold co-occurrence correlation value in relation to the primary event code in accordance with a cross-code occurrence relationship data object. The co-occurrence correlation value threshold may describe a threshold which, when exceeded by the two respective event codes, leads to an inference that the event codes are similar. The code co-occurrence inference machine learning model may be configured to, for each secondary event code in a defined-size subset, determine a per-code similar subset of the plurality of secondary event codes by mapping secondary event code embeddings for the secondary event codes in the defined-size subset to a multi-dimensional space and calculating cross-embedding distances.

The term "co-occurrence correlation value" may refer to a data object describing a degree of historical correlation between a corresponding primary event code and a corresponding secondary event code (e.g., between a medical claim code and a pharmaceutical claim code). The co-occurrence correlation values may be stored in a cross-code occurrence relationship data object (e.g., a co-occurrence matrix).

The term "cross-code occurrence relationship data object" may refer to a data object that describes the cross-occurrence correlation values between a group of primary event codes and a group of secondary event codes (e.g., between a group of medical claim codes and a group of pharmaceutical claim does). The cross-code occurrence relationship data object may comprise a co-occurrence matrix describing a plurality of co-occurrence correlation values. The cross-code occurrence relationship data object may be used to determine the n most co-occurring secondary event codes with respect to a primary event code, which are then used to generate a defined-size subset of secondary event codes for the primary event code.

The term "code embedding machine learning model" may refer to a data object that describes steps/operations and/or parameters of a machine learning model that is configured generate an embedding with respect to an event code. For example, the code embedding machine learning model may be configured to process a secondary event code in order to generate a secondary event code embedding for the secondary event code in relation to a primary event code. An example of a code embedding machine learning model is a convolutional neural network model, a Global Vectors for Word Representation (GloVe) machine learning model, a Word2Vec machine learning model, an autoencoder model, a convolutional-network-based encoder model, a recurrent-neural-network-based encoder model and/or the like.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware framework and/or operating system platform. A software component comprising assembly language instructions may require conversion into executable machine code by an assembler prior to execution by the hardware framework and/or platform. Another example programming language may be a higher-level programming language that may be portable across multiple frameworks. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatuses, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Framework

FIG. 1 is a schematic diagram of an example system architecture 100 for performing predictive data analysis steps/operations and generating corresponding user interface data (e.g., for providing and/or updating a user interface). The system architecture 100 includes a predictive data analysis system 101 comprising a predictive data analysis computing entity 106 configured to generate predictive outputs that lead to performing one or more prediction-based actions. The predictive data analysis system 101 may communicate with one or more external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The system architecture 100 includes a storage subsystem 108 configured to store at least a portion of the data utilized by the predictive data analysis system 101. The predictive data analysis computing entity 106 may be in communication with one or more external computing entities 102. The predictive data analysis computing entity 106 may be configured to receive requests and/or data from external computing entities 102, process the requests and/or data to generate predictive outputs (e.g., predictive data analysis data objects), and provide the predictive outputs to the external computing entities 102. The external computing entity 102 (e.g., management computing entity) may periodically update/provide raw input data (e.g., data objects describing primary events and/or secondary events) to the predictive data analysis system 101. The external computing entities 102 may further generate user interface data (e.g., one or more data objects) corresponding to the predictive outputs and may provide (e.g., transmit, send and/or the like) the user interface data corresponding with the predictive outputs for presentation to user computing entities operated by end-users.

The storage subsystem 108 may be configured to store at least a portion of the data utilized by the predictive data analysis computing entity 106 to perform predictive data analysis steps/operations and tasks. The storage subsystem 108 may be configured to store at least a portion of operational data and/or operational configuration data including operational instructions and parameters utilized by the predictive data analysis computing entity 106 to perform predictive data analysis steps/operations in response to requests. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. Such functions, steps/operations, and/or processes may include, for example, transmitting, receiving, operating on, processing, displaying, storing, determining, creating/generating, monitoring, evaluating, comparing, and/or similar terms used herein interchangeably. In one embodiment, these functions, steps/operations, and/or processes can be performed on data, content, information, and/or similar terms used herein interchangeably.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with a processing element 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include at least one non-volatile memory 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include at least one volatile memory 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include a network interface 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless client communication networks using any of a variety of protocols, such as general packet radio service (GPRS), Universal Mobile Telecommunications System (UMTS), Code Division Multiple Access 2000 (CDMA2000), CDMA2000 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, steps/operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1xRTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these frameworks and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

Described herein are various techniques for predictive data analysis steps/operations in relation to at least one primary event data object (e.g., a primary event data object related to a medical claim) and a plurality of secondary event data objects (e.g., a plurality of secondary event data objects related to a group of pharmacy claims). Some of the disclosed techniques may utilize one or more machine learning models to perform predictive data analysis steps/operations that lead to performing one or more prediction-based actions. Some of the described techniques utilize a particular configuration of machine learning models and/or layers. The output of a machine learning model and/or layers therein may be supplied as an input for subsequent steps/operations by another machine learning model and/or layer. However, a person of ordinary skill in the art will recognize that predictive data analysis steps/operations discussed herein may be performed using different combinations of machine learning models/techniques than the particular combinations described herein.

FIG. 4 provides a flowchart diagram illustrating an example process 400 for determining a related subset of a plurality of candidate secondary events with respect to a primary event having a primary event code, such that the related subset can be directly mapped to the primary event, as well as using the output of the noted mapping steps/operations to train a lifecycle inference machine learning model.

Beginning at step/operation 401, the predictive data analysis system 101 identifies a primary event (e.g., a medical claim entry) and a plurality of candidate secondary event types (e.g., pharmaceutical claim entries). An operational example of performing step/operation 401 is depicted in FIG. 5. As depicted in FIG. 5, step/operation 401 may be performed when the storage subsystem 108 provides a group of medical claims (i.e., Dx claims) and a group of pharmaceutical claims (i.e., Rx claims) to the predictive data analysis computing entity 106.

A primary event may describe a record of an occurred event in response to which occurred events pertaining to one or more secondary events occur. The primary event may be associated with a primary event timestamp indicating a timepoint associated with the primary event. An example primary event may be a recorded medical claim entry for a patient profile. The primary event may be associated with one or more primary event attributes, including a primary event code (e.g., a medical claim code, such as a diagnosis code, a procedure code, and/or the like).

In contrast, a secondary event may describe a record of an event occurring in response to a primary event. The secondary event may correspond with a secondary event timestamp, indicating a timepoint associated with the secondary event and occurring subsequent to the timepoint of a corresponding primary event timestamp. An example secondary event may be a data object describing a recorded pharmaceutical claim entry for a patient profile. A secondary event may be associated with one or more secondary event attributes including a secondary event code (e.g., a pharmaceutical claim code).

At step/operation 402, the predictive data analysis system 101 determines an inferred lifecycle for the primary event. The inferred lifecycle may describe a predicted time period for a primary event, where the predicted time period is estimated to include the secondary events associated with the primary event. In some embodiments, when a lifecycle inference machine learning model is deemed insufficiently trained (e.g., during an initial iteration of a predictive framework), the inferred lifecycle may be deemed to commence with a primary event timestamp and continue till a plurality of secondary events happen without a considerable time break (e.g., may terminate if there are no secondary events continuously for 45 days after the primary event timestamp). In some embodiments, when a lifecycle inference machine learning model is deemed sufficiently trained (e.g., during a post-initial iteration of a predictive framework), the inferred lifecycle may be determined by processing one or more lifecycle-related attributes for a corresponding primary event using a lifecycle inference machine learning model.

An operational example of performing step/operation 402 is depicted in FIG. 5. As depicted in FIG. 5, step/operation 402 may be performed by determining an inferred lifecycle for a medical claim. As described above, before a lifecycle inference machine learning model is deemed sufficiently trained (e.g., during an initial iteration of the predictive data analysis system 101), the inferred lifecycle for a medical claim may be determined as the period starting with the medical claim timestamp for the medical claim and terminating after an earliest continuous threshold time period without occurrence of secondary event codes and having a defined length following the medical claim timestamp. An operational example of such a static determination of an inferred lifecycle 402A for a medical claim is depicted in FIG. 6.

As depicted in FIG. 6, the predictive data analysis system 101 has determined that the medical claim D1 has an inferred lifecycle beginning with a corresponding medical claim timestamp of January 1st in January and terminating 90 days after the medical claim timestamp, when 45 days of lack of drug claim activity occurring following the timestamp associated with the medical claim D1. In some embodiments, instead of terminating after an earliest continuous threshold time period, the lifecycle of a primary event may terminate at a selected point-censored time. For example, as depicted in FIG. 6, the predictive data analysis system 101 has determined that the medical claim D2 has an inferred lifecycle beginning with a corresponding medical claim timestamp in mid-June and terminating at a depicted point-censored time in September. Thus, the inferred lifecycle for the medical claim is a 60 day period beginning in June and terminating in September.

As further noted above, when a lifecycle inference machine learning model is deemed sufficiently trained (e.g., during a post-initial iteration of a predictive framework), the inferred lifecycle may be determined by processing one or more lifecycle-related attributes for a corresponding primary event using a lifecycle inference machine learning model. The lifecycle inference machine learning model may describe steps/operations and/or parameters of a machine learning model that is configured to determine an inferred lifecycle (e.g., a time window, time-to-event and/or the like) with respect to a primary event (e.g., by processing one or more lifecycle-related attributes for the primary event). An example of a lifecycle inference machine learning model is an incident life machine learning model, a survival machine learning model, a time-to-event machine learning model, a regression-based proportional hazard machine learning model (e.g., Weibull model, Log-Normal model, Gamma model, Log-logistic model and/or the like), a convolutional neural network model and/or the like.

FIG. 7 provides an operational example illustrating training data 402B that can be used to train a lifecycle inference machine learning model. As depicted in FIG. 7, the exemplary training data 402B include a number of training data entries each associated with a row of the training data 402B, where each training data entry is associated with a group of predictor variables 701 as well as a ground-truth inferred lifecycle 702.

Returning to FIG. 4, at step/operation 403, the predictive data analysis system 101 determines a filtered subset of the plurality of candidate secondary event types for the primary event based at least in part on the inferred lifecycle for the primary event. The filtered subset may include one or more candidate secondary events, each associated with a candidate secondary event timestamp that falls within an inferred lifecycle corresponding with a primary event, where the one or more candidate secondary events are determined at least in part by performing one or more filtering steps/operations and/or matching steps/operations with respect to all of the candidate secondary events that fall within the inferred lifecycle. Example filtering steps/operations include, without limitation, time-based and/or attribute-based filtering steps/operations. Example matching techniques include, without limitation, Levenshtein fuzzy matching, Smith Waterman matching, ensemble-based matching and/or the like.

An operational example of performing step/operation 403 is depicted in FIG. 5. As depicted in FIG. 5, step/operation 403 may be performed by performing a time-based filtering 403-1 configured to determine the pharmacy claims whose timestamp falls within the inferred lifecycle for a primary medical claim and subsequently performing a prescriber-based filtering 403-2 on the output of the time-based filtering 403-1 by filtering out pharmacy claims that are not associated with the prescriber/(or)specialty/(or)institution/(or)location of the primary medical claim.

FIG. 8 provides an operational example of time-based filtering steps/operations in accordance with some embodiments discussed herein. A timeline identifying a plurality of recorded medical claim entries for a patient profile, "CL-1," "CL-2," "CL-3," "CL-4," "CL-5," and a plurality of candidate recorded pharmaceutical claim entries, "RX-1," "RX-2," "RX-3," "RX-4," "RX-5," "RX-6," "RX-7," "RX-8," "RX-9," "RX-10" and "RX-11" is provided in FIG. 8. As depicted in FIG. 8, "CL-1" and "CL-2" are medical claim entries describing a fracture elbow and elbow stiches, respectively. Additionally, CL-1" and "CL-2" are associated with a primary event occurring on Day 7 and an inferred lifecycle beginning on Day 7 and terminating on Day 47. Medical claim entry "CL-3" describes an asthma check-up associated with a primary event occurring on Day 1. Medical claim entry "CL-4" describes an elbow bandage associated with the same primary event corresponding with "CL-1" occurring on Day 30 and an inferred lifecycle beginning on Day 30 and terminating on Day 73. Medical claim entry "CL-5" describes an asthma checkup associated with the same primary event corresponding with "CL-3" and occurring on Day 72. Based at least in part on one or more time-based filtering steps/operations, a filtered subset of the plurality of candidate secondary events (i.e., "RX-1," "RX-2," "RX-3," "RX-4," "RX-5," "RX-6," "RX-7," "RX-8," "RX-9," "RX-10" and "RX-11") corresponding with each of the recorded medical claim entries (i.e., "CL-1," "CL-2," "CL-3," "CL-4" and "CL-5") is identified. Each candidate secondary event in the filtered subset is associated with a candidate secondary event timestamp that falls within the inferred lifecycle. For example, as shown "CL-1" and "CL-2" are associated with a filtered subset comprising "RX-1," "RX-2," "RX-3," "RX-4," "RX-5," "RX-6," "RX-7," "RX-8," and "RX-9." "CL-3" is associated with a filtered subset comprising "RX-7," "RX-8," "RX-9," "RX-10" and "RX-11."

As noted above, in addition to time-based filtering steps/operations, the predictive data analysis system 101 may also be configured to perform attribute-based filtering steps/operations (e.g., attribute-based matching steps/operations). Example matching techniques include, without limitation, Levenshtein fuzzy matching, Smith Waterman matching, ensemble-based matching and/or the like.

FIG. 9 provides an operational example of prescriber-based filtering steps/operations in accordance with some embodiments disclosed herein. As illustrated in FIG. 9, the predictive data analysis system 101 uses as input the filtered subset determined using time-based filtering steps/operations illustrated in FIG. 8. Each of the medical claim entries, "CL-1," "CL-2," "CL-3," and "CL-4," is associated with additional lifecycle-related attributes (e.g., medical claim attributes). As further illustrated in FIG. 9, each of the medical claim entries, "CL-1," "CL-2," "CL-3," and "CL-4," is associated with various medical claim attributes, i.e., a diagnosis and a Provider or Provider Name. Additionally, each of the pharmaceutical claim entries, "RX-1," "RX-2," and "RX-3," is associated with various pharmaceutical claim attributes, i.e., medication information and prescriber information. The predictive data analysis system 101 may perform prescriber-based filtering steps/operations in order to further filter the time-based filtered subset. As illustrated in FIG. 9, based at least in part on the prescriber-based filtering steps/operations (e.g., by correlating/matching at least a portion of the medical and pharmaceutical claim attributes), "CL-1" and "CL-2" are associated with "RX-1," "RX-2," "RX-3," "RX-7," "RX-8," and "RX-9," "CL-3" is associated with "RX-7," "RX-8," and "RX-11."

Returning to FIG. 4, at step/operation 404, the predictive data analysis system 101 determines a most co-occurring subset of a plurality of secondary event codes for the filtered subset. The most co-occurring subset can comprise one or more secondary event codes having the most co-occurring attributes with respect to one or more primary event codes. In some embodiments, the predictive data analysis system 101 may process the secondary event codes in the filtered subset using a code co-occurrence inference machine learning model in order to generate the most co-occurring subset. The code co-occurrence inference machine learning model may comprise steps/operations and/or parameters of a machine learning model that is configured to process one or more primary event codes in order to detect a most co-occurring subset of a plurality of secondary event codes having similar attributes with respect to the one or more primary event codes.

In some embodiments, performing the step/operation 404 comprises: (i) determining a defined-size subset of a plurality of secondary event codes, wherein each secondary event code in the defined-size subset is deemed to have an above-threshold co-occurrence correlation value in relation to the primary event code in accordance with a cross-code occurrence relationship data object; (ii) for each secondary event code of the plurality of secondary event codes that is in the defined-size subset, determining a per-code similar subset of the plurality of secondary event codes, and (iii) determining the most co-occurring subset to comprise each candidate secondary event of the plurality of candidate secondary events whose respective candidate secondary event code is in the per-code similar subset for a secondary event code of the plurality of secondary event codes as well as each secondary event code in the defined-size subset.

An operational example of performing step/operation 404 is depicted in FIG. 5. As depicted in FIG. 5, step/operation 404 can be performed by performing the following steps/operations: (i) at step/operation 404-1, using a medical-claim-pharmacy-claim co-occurrence matrix 501 (which is an example of a cross-code occurrence relationship data object) to determine a defined-size subset of the pharmaceutical claim codes that are deemed to have above-threshold co-occurrence correlation values in relation to a particular medical claim, and (ii) at step/operation 404-2, processing each pharmaceutical claim code in the defined-size subset using a code co-occurrence inference machine learning model to determine a per-code similar subset for the pharmaceutical claim code. The per-code similar subsets for the pharmaceutical claim codes as well as the defined-size subset may then be combined to form the most co-occurring subset of the pharmaceutical claim codes for the medical claim.

At step/operation 404-1, the medical-claim-pharmacy-claim co-occurrence matrix 501 is utilized to determine a defined-size (e.g., size five) subset of a group of pharmaceutical claim codes that are deemed to have an above-threshold co-occurrence correlation values in relation to a particular medical claim code. For example, in accordance with the medical-claim-pharmacy-claim co-occurrence matrix 501 of FIG. 10, given a threshold co-occurrence correlation value of two, pharmaceutical claim codes RxUI-1 and RxUI-2 may be deemed to have an above-threshold co-occurrence correlation in relation to the medical claim code ICD-1, and thus the defined-size subset of the pharmaceutical claim codes for the medical claim code ICD-1 may consist of the pharmaceutical claim codes RxUI-1 and RxUI-2.

The medical-claim-pharmacy-claim co-occurrence matrix 501 is an example of a cross-code occurrence relationship data object. The cross-code occurrence relationship data object may describe the cross-occurrence correlation values between a group of primary event codes and a group of secondary event codes (e.g., between a group of medical claim codes and a group of pharmaceutical claim does). The cross-code occurrence relationship data object may comprise a co-occurrence matrix describing a plurality of co-occurrence correlation values. The cross-code occurrence relationship data object may be used to determine the n most co-occurring secondary event codes with respect to a primary event code, which are then used to generate a defined-size subset of secondary event codes for the primary event code (with n being the defined size of the defined-size subset). Each co-occurrence correlation value described by the cross-code occurrence relationship data object may in turn describe a degree of historical correlation between a corresponding primary event code and a corresponding secondary event code (e.g., between a medical claim code and a pharmaceutical claim code).

At step/operation 404-2, each pharmaceutical claim code is processed using a code embedding machine learning model to generate a pharmaceutical claim code embedding for the pharmaceutical claim code. Afterward, the generated pharmaceutical claim code embeddings are mapped to a multi-dimensional space of a code co-occurrence inference machine learning model, and the cross-embedding distance between pharmaceutical claim code embeddings for the pharmaceutical claim codes in the defined-size subset and the pharmaceutical claim code embeddings for the pharmaceutical claim code that are not in the defined-size subset are calculated. The per-code similar subset for each pharmaceutical claim code in the defined-size subset is generated based at least in part on the pharmaceutical claim codes whose corresponding pharmaceutical claim code embeddings have a below-threshold cross-embedding displace with respect to the pharmaceutical claim code embedding for the pharmaceutical claim code that is in the defined-size subset. The per-code similar subsets for the pharmaceutical claim codes in the defined-size subset are then combined to generate a portion of the most co-occurring subset of the pharmaceutical claim codes for the medical claim.

For example, assume that the defined-size subset of the pharmaceutical claim codes for the medical claim code ICD-1 consists of the pharmaceutical claim codes RxUI-1 and RxUI-2. Assume further that, when mapped to a multi-dimensional space using pharmaceutical claim code embeddings, the pharmaceutical claim code embedding of the pharmaceutical claim code RxUI-4 is deemed to have a below-threshold cross-embedding distance with respect to the pharmaceutical claim code embedding for the pharmaceutical claim code RxUI-1, and the pharmaceutical claim code embeddings of the pharmaceutical claim codes RxUI-6 and RxUI-8 is deemed to have a below-threshold cross-embedding distance with respect to the pharmaceutical claim code embedding for the pharmaceutical claim code RxUI-2. In this example: (i) the per-code similar subset for the pharmaceutical claim code is RxUI-1 consists of the pharmaceutical claim code RxUI-4, (ii) the per-code similar subset for the pharmaceutical claim code is RxUI-2 consists of the pharmaceutical claim codes RxUI-6 and RxUI-8, and (iii) the most co-occurring subset for the medical claim code ICD-1 consists of the pharmaceutical claim codes RxUI-1, RxUI-2, RxUI-4, RxUI-6, and RxUI-8.

An operational example of a multi-dimensional mapping space 1100 that can be used to generate the per-code similar subsets for OxyContin, Gabapentin, Lidocaine, and Acetaminophen is depicted in FIG. 11. In FIG. 11, four data outputs representing pairings describing drugs (and corresponding pharmaceutical codes) that are sufficiently similar to one another are shown. The code embedding machine learning model has determined that each data output pair (e.g., OxyContin/Roxicodone, Gabapentin/Pregabalin, Lidocaine/Bupivacaine and Acetaminophen/Ibuprofen) is sufficiently similar with respect to an associated medical claim record such that it can be inferred that each pair of drugs is prescribed under similar circumstances. In other words, a distance measure between each pair of drugs and/or pharmaceutical codes is evaluated in relation to a threshold distance measure that, when satisfied, leads to an inference that the two data drugs and/or pharmaceutical codes are sufficiently similar.

The multi-dimensional space depicted in FIG. 11 is an example of a multi-dimensional space associated with a code co-occurrence inference machine learning model. The code co-occurrence inference machine learning model may be a machine learning model that is configured to process one or more secondary event codes in order to detect a subset of a plurality of secondary event codes having similar attributes with respect to the one or more primary event codes. In some embodiments, the code co-occurrence inference machine learning model is first configured to determine a defined-size subset of a plurality of secondary event codes (e.g., a subset of three most co-occurring secondary event codes), wherein each secondary event code in the defined-size subset is deemed to have an above-threshold co-occurrence correlation value in relation to the primary event code in accordance with a cross-code occurrence relationship data object. The co-occurrence correlation value threshold may describe a threshold which, when exceeded by the two respective event codes, leads to an inference that the event codes are similar. The code co-occurrence inference machine learning model may be configured to, for each secondary event code in a defined-size subset, determine a most co-occurring subset of the plurality of secondary event codes by mapping secondary event code embeddings for the secondary event codes in the defined-size subset to a multi-dimensional space and calculating cross-embedding distances.

To generate secondary event code embedding for a secondary event code, the code co-occurrence inference machine learning model may cause a code embedding machine learning model to process the secondary event code. The code embedding machine learning model may be a machine learning model that is configured generate an embedding with respect to an event code. For example, the code embedding machine learning model may be configured to process a secondary event code in order to generate a secondary event code embedding for the secondary event code in relation to a primary event code. An example of a code embedding machine learning model is a convolutional neural network model, a Global Vectors for Word Representation (GloVe) machine learning model, a Word2Vec machine learning model, an autoencoder model, a convolutional-network-based encoder model, a recurrent-neural-network-based encoder model and/or the like.

Returning to FIG. 4, at step/operation 405, the predictive data analysis system 101 determines a related subset of the candidate secondary event types based at least in part on the filtered subset and the most co-occurring subset. For example, the related subset may be based at least in part on each candidate secondary event of the plurality of candidate secondary events that is in the filtered subset and is associated with a candidate secondary event code that falls within the most co-occurring subset. An operational example of performing step/operation 405 is depicted in FIG. 5. As depicted in FIG. 5, step/operation 405 can be performed by identifying each pharmaceutical claim that is both in the output of the steps/operations 404-2 and whose pharmaceutical claim code is in the output of the operation 404-2, and including the identified pharmaceutical claims among the related subset for the medical claim.

Returning to FIG. 4, at step/operation 406, the predictive data analysis system 101 performs one or more prediction-based actions (e.g., determine whether the lifecycle inference machine learning model is sufficiently trained) based at least in part on the determined related subset. The related subset can describe one or more secondary events identified from a plurality of candidate secondary events. The one or more secondary events comprise secondary event codes describing one or more attributes/criteria that are sufficiently similar to and/or satisfies a joint criteria threshold in relation to a corresponding primary event code. The related subset is determined based at least in part by performing the above-detailed steps/operations described in steps/operations 402, 403, 404, 405 in order to correlate one or more secondary events of the plurality of candidate secondary events with the corresponding primary event.

In various embodiments, the predictive data analysis system 101 may be configured to respond to queries for and/or trigger generation (e.g., by an external computing entity 102) of user interface data (e.g., messages, data objects and/or the like) corresponding with predictive outputs. An external computing entity 102 may provide the user interface data for presentation by a user computing entity. The user interface data may correspond with an associated workflow and or one or more queues generated for presentation to an end user.

A queue may refer to an ordering of a plurality of data objects describing primary events and corresponding secondary events based at least in part on a portion of the predictive outputs described herein. In some embodiments, predictive data analysis system 101 may be configured to generate one or more API-based data objects corresponding with at least a portion of the predictive outputs and/or the one or more queues. The predictive data analysis system 101 may provide (e.g., transmit, send) the one or more API-based data objects representing at least a portion of the predictive outputs and/or the one or more queues to an end user interface (e.g., an investigation agent user interface) for display and/or further steps/operations. The predictive outputs may be used to dynamically update the user interface (e.g., an investigation agent user interface), or generate alerts for load balancing steps/operations or for determining a distribution of resources with respect to a healthcare services inventory (e.g., assigning portions of inventory or data subsets to a plurality of investigative agents).

FIG. 12 provides an operational example showing a prediction output user interface 1200 that may be generated based at least in part on user interface data which are in turn generated based at least in part on the above-described predictive outputs. The external computing entity 102 may generate the user interface data and provide (e.g., transmitted, sent and/or the like) corresponding user interface data for presentation by the prediction output user interface 1200. The user interface data may be used for dynamically updating the prediction output user interface 1200. In some embodiments, the prediction output user interface 1200 may dynamically update the display on a continuous or regular basis or in response to certain triggers.

As depicted in FIG. 12, the user interface data may describe a medical claim entry and corresponding pharmaceutical claim entries associated with a patient profile. The patient profile can be a data object storing and/or providing access to patient information/data. The patient record/profile may also comprise member information/data, patient features, and/or similar words used herein interchangeably that can be associated with a given member, claim, and/or the like. In some embodiments, patient information/data can include age, gender, poverty rates, known health conditions, home location, profession, access to medical care, medical history, claim history, patient identifier (ID), and/or the like. Patient information/data may also include marital status, employment status, employment type, socioeconomic information/data (e.g., income information/data), relationship to the primary insured, insurance product information/data, insurance plan information/data, member classifications, language information/data, and/or the like.

The prediction output user interface 1200 may comprise various features and functionalities for accessing, and/or viewing user interface data. The prediction output user interface 1200 may also comprise messages to an end-user in the form of banners, headers, notifications, and/or the like. As will be recognized, the described elements are provided for illustrative purposes and are not to be construed as limiting the dynamically updatable interface in any way.

At step/operation 407, the predictive data analysis system 101 trains the lifecycle inference machine learning model based at least in part on the related subset. In some embodiments, the predictive data analysis system 101 determines a period of time comprising the timestamps of each secondary event code in the related subset as a ground-truth inferred lifecycle, and uses the ground-truth inferred lifecycle to generate training data used to train the lifecycle inference machine learning model.

An operational example of performing step/operation 407 is depicted in FIG. 5. As depicted in FIG. 5, step/operation 407 can be performed by determining the ground-truth inferred lifecycle for a particular medical claim based at least in part on the timestamp for each pharmaceutical claim that falls within the related subset for the particular medical claim, and using the determined ground-truth inferred lifecycle to train the lifecycle inference machine learning model. For example, if the timestamps for pharmaceutical claims that are deemed related to a medical claim include Jan. 1, 2019, Jan. 2, 2019, and Feb. 1, 2019, the predictive data analysis system 101 may determine that the medical claim is associated with the ground-truth inferred lifecycle Jan. 1, 2019-Feb. 1, 2019, and use this determined ground-truth inferred lifecycle to retrain the lifecycle inference machine learning model.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method comprising:
processing, by one or more processors, one or more lifecycle-related attributes for a primary event code using a lifecycle inference machine learning model to generate an inferred lifecycle for a primary event;
determining, by the one or more processors, a filtered subset of a plurality of candidate secondary events, wherein each candidate secondary event in the filtered subset is associated with a candidate secondary event timestamp that falls within the inferred lifecycle;
processing, by the one or more processors, the primary event code using a code co-occurrence inference machine learning model to identify a most co-occurring subset of a plurality of secondary event codes for the primary event;
determining, by the one or more processors, a related subset of the plurality of candidate secondary events based at least in part on each candidate secondary event of the plurality of candidate secondary events that is in the filtered subset and is associated with a candidate secondary event code that falls within the most co-occurring subset;
determining, by the one or more processors, a ground-truth inferred lifecycle for the primary event code based at least in part on the related subset, wherein the ground-truth inferred lifecycle comprises one or more candidate secondary event timestamps for one or more candidate secondary events of the plurality of candidate secondary events that is in the related subset; and
training, by the one or more processors, the lifecycle inference machine learning model based at least in part on the ground-truth inferred lifecycle.

2. The computer-implemented method of claim 1, further comprising:
determining, by the one or more processors, whether the lifecycle inference machine learning model is deemed insufficiently trained, and
in response to determining that the lifecycle inference machine learning model is deemed insufficiently trained:
detecting, by the one or more processors, an earliest continuous threshold time period after a primary event timestamp of the primary event code that does not comprise any candidate secondary event timestamp for each candidate secondary event of the plurality of candidate secondary events, and
determining, by the one or more processors, that the inferred lifecycle comprises an inferred time period that begins with the primary event timestamp and terminates at a timepoint associated with the earliest continuous threshold time period.

3. The computer-implemented method of claim 1, further comprising:
determining, by the one or more processors and using the code co-occurrence inference machine learning model, a defined-size subset of the plurality of secondary event codes, wherein each secondary event code in the defined-size subset is deemed to have an above-threshold co-occurrence correlation value in relation to the primary event code in accordance with a cross-code occurrence relationship data object,
for each secondary event code of the plurality of secondary event codes that is in the defined-size subset, determining, by the one or more processors and using the code co-occurrence inference machine learning model, a per-code similar subset of the plurality of secondary event codes, and
determining, by the one or more processors and using the code co-occurrence inference machine learning model, the most co-occurring subset to comprise each candidate secondary event of the plurality of candidate secondary events whose respective candidate secondary event code is in the per-code similar subset for a secondary event code of the plurality of secondary event codes.

4. The computer-implemented method of claim 3, wherein determining the per-code similar subset comprises:
for each secondary event code of the plurality of secondary event codes,
processing, by the one or more processors, the secondary event code using a code embedding machine learning model for a primary event code type to generate a secondary event code embedding for the secondary event code in relation to the primary event code, and
determining, by the one or more processors, a cross-embedding distance for the secondary event code based at least in part on the secondary event code embedding for the secondary event code; and
determining, by the one or more processors, the per-code similar subset based at least in part on each cross-embedding distance for the secondary event code of the plurality of secondary event codes.

5. The computer-implemented method of claim 4, wherein the code embedding machine learning model is trained in accordance with a plurality of co-occurrence correlation values described by the cross-code occurrence relationship data object.

6. The computer-implemented method of claim 1, wherein the primary event describes a recorded medical claim entry for a patient profile.

7. The computer-implemented method of claim 1, wherein the plurality of candidate secondary events describe a plurality of recorded pharmaceutical claim entries for a patient profile.

8. A computing system comprising memory and one or more processors communicatively coupled to the memory, the one or more processors configured to:
process one or more lifecycle-related attributes for a primary event code using a lifecycle inference machine learning model to generate an inferred lifecycle for a primary event;
determine a filtered subset of a plurality of candidate secondary events, wherein each candidate secondary event in the filtered subset is associated with a candidate secondary event timestamp that falls within the inferred lifecycle;
process the primary event code using a code co-occurrence inference machine learning model to identify a most co-occurring subset of a plurality of secondary event codes for the primary event;
determine a related subset of the plurality of candidate secondary events based at least in part on each candidate secondary event of the plurality of candidate secondary events that is in the filtered subset and is associated with a candidate secondary event code that falls within the most co-occurring subset;
determine a ground-truth inferred lifecycle for the primary event code based at least in part on the related subset, wherein the ground-truth inferred lifecycle comprises one or more candidate secondary event timestamps for one or more candidate secondary events of the plurality of candidate secondary events that is in the related subset; and
train the lifecycle inference machine learning model based at least in part on the ground-truth inferred lifecycle.

9. The computing system of claim 8, wherein the one or more processors are further configured to:
determine whether the lifecycle inference machine learning model is deemed insufficiently trained, and
in response to determining that the lifecycle inference machine learning model is deemed insufficiently trained:
detect an earliest continuous threshold time period after a primary event timestamp of the primary event code that does not comprise any candidate secondary event timestamp for each candidate secondary event of the plurality of candidate secondary events, and
determine that the inferred lifecycle comprises an inferred time period that begins with the primary event timestamp and terminates at a timepoint associated with the earliest continuous threshold time period.

10. The computing system of claim 8, wherein the code co-occurrence inference machine learning model is configured to:
determine a defined-size subset of the plurality of secondary event codes, wherein each secondary event code in the defined-size subset is deemed to have an above-threshold co-occurrence correlation value in relation to the primary event code in accordance with a cross-code occurrence relationship data object,
for each secondary event code of the plurality of secondary event codes that is in the defined-size subset, determine a per-code similar subset of the plurality of secondary event codes, and
determine the most co-occurring subset to comprise each candidate secondary event of the plurality of candidate secondary events whose respective candidate secondary event code is in the per-code similar subset for a secondary event code of the plurality of secondary event codes.

11. The computing system of claim 10, wherein the one or more processors are further configured to:
for each secondary event code of the plurality of secondary event codes,
process the secondary event code using a code embedding machine learning model for a primary event code type to generate a secondary event code embedding for the secondary event code in relation to the primary event code, and
determine a cross-embedding distance for the secondary event code based at least in part on the secondary event code embedding for the secondary event code; and
determine the per-code similar subset based at least in part on each cross-embedding distance for the secondary event code of the plurality of secondary event codes.

12. The computing system of claim 11, wherein the code embedding machine learning model is trained in accordance with a plurality of co-occurrence correlation values described by the cross-code occurrence relationship data object.

13. One or more non-transitory computer-readable storage media including instructions that, when executed by one or more processors, cause the one or more processors to:
process one or more lifecycle-related attributes for a primary event code using a lifecycle inference machine learning model to generate an inferred lifecycle for a primary event;
determine a filtered subset of a plurality of candidate secondary events, wherein each candidate secondary event in the filtered subset is associated with a candidate secondary event timestamp that falls within the inferred lifecycle;
process the primary event code using a code co-occurrence inference machine learning model to identify a most co-occurring subset of a plurality of secondary event codes for the primary event;
determine a related subset of the plurality of candidate secondary events based at least in part on each candidate secondary event of the plurality of candidate secondary events that is in the filtered subset and is associated with a candidate secondary event code that falls within the most co-occurring subset;
determine a ground-truth inferred lifecycle for the primary event code based at least in part on the related subset, wherein the ground-truth inferred lifecycle comprises one or more candidate secondary event timestamps for one or more candidate secondary events of the plurality of candidate secondary events that is in the related subset; and
train the lifecycle inference machine learning model based at least in part on the ground-truth inferred lifecycle.

14. The one or more non-transitory computer-readable storage media of claim 13, the instructions, when executed by one or more processors, further cause the one or more processors to:
determine whether the lifecycle inference machine learning model is deemed insufficiently trained, and
in response to determining that the lifecycle inference machine learning model is deemed insufficiently trained:
detect an earliest continuous threshold time period after a primary event timestamp of the primary event code that does not comprise any candidate secondary event timestamp for each candidate secondary event of the plurality of candidate secondary events, and
determine that the inferred lifecycle comprises an inferred time period that begins with the primary event timestamp and terminates at a timepoint associated with the earliest continuous threshold time period.

15. The one or more non-transitory computer-readable storage media of claim 13, wherein the code co-occurrence inference machine learning model is configured to:
- determine a defined-size subset of the plurality of secondary event codes, wherein each secondary event code in the defined-size subset is deemed to have an above-threshold co-occurrence correlation value in relation to the primary event code in accordance with a cross-code occurrence relationship data object,
- for each secondary event code of the plurality of secondary event codes that is in the defined-size subset, determine a per-code similar subset of the plurality of secondary event codes, and
- determine the most co-occurring subset to comprise each candidate secondary event of the plurality of candidate secondary events whose respective candidate secondary event code is in the per-code similar subset for a secondary event code of the plurality of secondary event codes.

16. The one or more non-transitory computer-readable storage media of claim 15, wherein the instructions, when executed by the one or more processors, further cause the one or more processors to:
- for each secondary event code of the plurality of secondary event codes,
  - processing the secondary event code using a code embedding machine learning model for a primary event code type to generate a secondary event code embedding for the secondary event code in relation to the primary event code, and
  - determining a cross-embedding distance for the secondary event code based at least in part on the secondary event code embedding for the secondary event code; and
- determining the per-code similar subset based at least in part on each cross-embedding distance for the secondary event code of the plurality of secondary event codes.

17. The one or more non-transitory computer-readable storage media of claim 16, wherein the code embedding machine learning model is trained in accordance with a plurality of co-occurrence correlation values described by the cross-code occurrence relationship data object.

\* \* \* \* \*